US012564471B2

(12) United States Patent
Geric et al.

(10) Patent No.: US 12,564,471 B2
(45) Date of Patent: Mar. 3, 2026

(54) AUGMENTED-REALITY ENDOSCOPIC VESSEL HARVESTING

(71) Applicant: TERUMO CARDIOVASCULAR SYSTEMS CORPORATION, Ann Arbor, MI (US)

(72) Inventors: Joseph Mark Geric, Livonia, MI (US); Takeshi Tsubouchi, Dexter, MI (US); Randal James Kadykowski, South Lyon, MI (US); Tatsunori Fujii, Bear, DE (US)

(73) Assignee: Terumo Cardiovascular Systems Corporation, Ann Arbor, MI (US)

( * ) Notice: Subject to any disclaimer, the term of this patent is extended or adjusted under 35 U.S.C. 154(b) by 35 days.

(21) Appl. No.: 17/399,225

(22) Filed: Aug. 11, 2021

(65) Prior Publication Data

US 2023/0053189 A1 Feb. 16, 2023

(51) Int. Cl.
A61B 90/00 (2016.01)
A61B 1/00 (2006.01)
(Continued)

(52) U.S. Cl.
CPC ............ A61B 90/37 (2016.02); A61B 1/0005 (2013.01); A61B 1/00087 (2013.01);
(Continued)

(58) Field of Classification Search
CPC ... A61B 90/37; A61B 1/0005; A61B 1/00087; A61B 1/00193; A61B 1/00194;
(Continued)

(56) References Cited

U.S. PATENT DOCUMENTS 6,892,090 B2 * 5/2005 Verard ................... A61B 90/36
600/427
7,331,971 B2 2/2008 Kashara et al.
(Continued)

FOREIGN PATENT DOCUMENTS

EP 2997926 B1 4/2019

OTHER PUBLICATIONS

Schmalz et al., "An endoscopic 3D scanner based on structured light", 2012, Medical Image Analysis, pp. 1063-1072 (Year: 2012).*

(Continued)

*Primary Examiner* — Adil Partap S Virk
(74) *Attorney, Agent, or Firm* — Fish & Richardson P.C.

(57) ABSTRACT

An endoscopic vessel harvesting system for surgical removal of a blood vessel to be used for coronary bypass uses endoscopic instruments for isolating and severing the vessel. An endoscopic camera in the endoscopic instruments captures images from a distal tip of the instrument within a dissected tunnel around the vessel. An image processor assembles a three-dimensional model of the tunnel from a series of images captured by the endoscopic camera. An augmented-reality display coupled to the image processor renders (e.g., visibly displays to the user in their field of view) a consolidated map representing the three-dimensional model along with a marker in association with the map indicating a current location of the distal tip.

12 Claims, 11 Drawing Sheets

(51) Int. Cl.

| | |
|---|---|
| *A61B 5/00* | (2006.01) |
| *A61B 34/20* | (2016.01) |
| *G06T 7/593* | (2017.01) |
| *G06T 17/00* | (2006.01) |
| *G06T 19/00* | (2011.01) |

(52) U.S. Cl.
CPC ...... *A61B 1/00193* (2013.01); *A61B 1/00194* (2022.02); *A61B 5/489* (2013.01); *A61B 34/20* (2016.02); *G06T 7/593* (2017.01); *G06T 17/00* (2013.01); *G06T 19/006* (2013.01); *A61B 2034/2063* (2016.02); *A61B 2090/365* (2016.02); *A61B 2090/367* (2016.02); *G06T 2207/10028* (2013.01); *G06T 2207/10068* (2013.01); *G06T 2207/30101* (2013.01); *G06T 2219/004* (2013.01)

(58) Field of Classification Search
CPC . A61B 5/489; A61B 34/20; A61B 2034/2063; A61B 2090/365; A61B 2090/367; G06T 7/593; G06T 17/00; G06T 19/006; G06T 2207/10028; G06T 2207/10068; G06T 2207/30101; G06T 2219/004
See application file for complete search history.

(56) References Cited

U.S. PATENT DOCUMENTS

| | | | |
|---|---|---|---|
| 8,048,100 B2 | 11/2011 | Kadykowski et al. | |
| 9,360,934 B2 | 6/2016 | Ruiz Morales et al. | |
| 9,474,580 B2 | 10/2016 | Hannaford et al. | |
| 9,646,423 B1 | 5/2017 | Sun et al. | |
| 9,858,387 B2* | 1/2018 | Lavi | G16H 50/50 |
| 9,861,446 B2 | 1/2018 | Lang | |
| 9,918,681 B2* | 3/2018 | Wallace | A61B 8/4218 |
| 9,980,780 B2 | 5/2018 | Lang | |
| 10,092,355 B1 | 10/2018 | Hannaford et al. | |
| 10,149,958 B1* | 12/2018 | Tran | G16H 50/20 |
| 10,152,789 B2 | 12/2018 | Carnes et al. | |
| 10,299,698 B2* | 5/2019 | Duindam | A61B 5/00 |
| 10,426,345 B2 | 10/2019 | Shekhar et al. | |
| 10,492,671 B2* | 12/2019 | Carroll | A61B 5/0071 |
| 10,624,663 B1 | 4/2020 | Barral et al. | |
| 11,147,635 B1* | 10/2021 | Sganga | G16H 20/40 |
| 11,191,423 B1* | 12/2021 | Zingaretti | G06T 19/00 |
| 12,011,163 B2* | 6/2024 | Shelton, IV | A61B 17/0686 |
| 2002/0068930 A1* | 6/2002 | Tasto | A61F 2/2493 |
| | | | 606/41 |
| 2003/0139649 A1* | 7/2003 | Kasahara | A61B 1/313 |
| | | | 600/157 |
| 2004/0111183 A1* | 6/2004 | Sutherland | A61B 34/76 |
| | | | 700/245 |
| 2004/0225185 A1* | 11/2004 | Obata | A61B 1/042 |
| | | | 600/118 |
| 2008/0009674 A1* | 1/2008 | Yaron | G06T 7/75 |
| | | | 600/117 |
| 2008/0085042 A1* | 4/2008 | Trofimov | G06T 17/00 |
| | | | 600/407 |
| 2008/0091171 A1* | 4/2008 | Strommer | G06T 7/564 |
| | | | 604/528 |
| 2008/0287803 A1* | 11/2008 | Li | A61B 8/5238 |
| | | | 382/128 |
| 2009/0204005 A1* | 8/2009 | Keast | A61B 1/018 |
| | | | 604/164.01 |
| 2010/0041942 A1* | 2/2010 | Okada | A61B 1/01 |
| | | | 600/37 |
| 2010/0249506 A1* | 9/2010 | Prisco | A61B 6/12 |
| | | | 600/117 |
| 2010/0249507 A1* | 9/2010 | Prisco | A61B 1/0002 |
| | | | 600/117 |
| 2010/0268067 A1* | 10/2010 | Razzaque | A61B 8/4245 |
| | | | 600/424 |
| 2010/0292533 A1 | 11/2010 | Kashara et al. | |
| 2011/0112362 A1* | 5/2011 | Minetoma | A61B 1/000094 |
| | | | 600/109 |
| 2011/0306986 A1 | 12/2011 | Lee et al. | |
| 2012/0035606 A1 | 2/2012 | Kano et al. | |
| 2012/0150048 A1* | 6/2012 | Kang | G06T 7/149 |
| | | | 600/481 |
| 2012/0188352 A1* | 7/2012 | Wittenberg | A61B 90/361 |
| | | | 348/E5.051 |
| 2012/0215094 A1* | 8/2012 | Rahimian | A61B 6/481 |
| | | | 600/414 |
| 2013/0041292 A1 | 2/2013 | Cunningham | |
| 2014/0022283 A1* | 1/2014 | Chan | H04N 9/3185 |
| | | | 345/633 |
| 2014/0343571 A1* | 11/2014 | Popovic | A61K 47/26 |
| | | | 606/130 |
| 2015/0073265 A1* | 3/2015 | Popovic | A61B 5/066 |
| | | | 600/424 |
| 2015/0112126 A1* | 4/2015 | Popovic | A61F 2/062 |
| | | | 600/102 |
| 2015/0141808 A1* | 5/2015 | Elhawary | A61B 5/7264 |
| | | | 600/424 |
| 2015/0164592 A1* | 6/2015 | Elhawary | A61B 5/0084 |
| | | | 600/479 |
| 2015/0272423 A1* | 10/2015 | Ito | A61B 1/2676 |
| | | | 600/476 |
| 2016/0183841 A1* | 6/2016 | Duindam | A61B 90/361 |
| 2016/0317171 A1* | 11/2016 | Orphanos | A61B 17/3205 |
| 2016/0331475 A1* | 11/2016 | Popovic | A61B 1/0016 |
| 2017/0007350 A1* | 1/2017 | Popovic | A61B 34/10 |
| 2017/0042521 A1* | 2/2017 | Popovic | A61B 17/22012 |
| 2017/0172663 A1* | 6/2017 | Popovic | A61B 90/361 |
| 2017/0202543 A1* | 7/2017 | Herdina | A61B 1/2676 |
| 2017/0245922 A1* | 8/2017 | Fujii | A61B 18/1445 |
| 2017/0251932 A1* | 9/2017 | Kaku | A61B 5/1071 |
| 2017/0367771 A1 | 12/2017 | Tako et al. | |
| 2018/0214214 A1* | 8/2018 | Reinstein | A61B 5/066 |
| 2018/0271603 A1 | 9/2018 | Nir et al. | |
| 2018/0279852 A1* | 10/2018 | Rafii-Tari | A61B 1/2676 |
| 2018/0310811 A1 | 11/2018 | Meglan et al. | |
| 2018/0368929 A1* | 12/2018 | Popovic | A61B 17/00234 |
| 2019/0008595 A1* | 1/2019 | Popovic | A61B 34/20 |
| 2019/0231444 A1* | 8/2019 | Tojo | A61B 1/0005 |
| 2020/0054399 A1* | 2/2020 | Duindam | A61B 1/00172 |
| 2020/0188033 A1* | 6/2020 | Komp | A61B 1/00172 |
| 2020/0226758 A1 | 7/2020 | Carnes et al. | |
| 2020/0281454 A1* | 9/2020 | Refai | A61B 1/00193 |
| 2021/0137350 A1* | 5/2021 | Inglis | A61B 1/0051 |
| 2022/0047317 A1* | 2/2022 | Yatawatta | A61M 25/10 |
| 2022/0054116 A1* | 2/2022 | Ikeda | A61B 17/00008 |
| 2022/0104694 A1* | 4/2022 | Shelton, IV | A61B 34/37 |
| 2022/0202500 A1* | 6/2022 | Ninni | A61B 1/00149 |
| 2022/0346751 A1* | 11/2022 | Donhowe | A61B 17/00234 |
| 2022/0354380 A1* | 11/2022 | Tata | G06T 19/20 |
| 2023/0044620 A1* | 2/2023 | Shochat | G06T 7/0012 |
| 2023/0117954 A1* | 4/2023 | Mino | G16H 40/63 |
| | | | 600/424 |
| 2023/0138666 A1* | 5/2023 | Husta | A61B 1/2676 |
| | | | 600/117 |
| 2023/0172593 A1* | 6/2023 | Gallagher | A61B 17/02 |
| | | | 600/210 |

OTHER PUBLICATIONS

Healthline, Endoscopy, 2012 Link: https://web.archive.org/web/20120927024113/https://www.healthline.com/health/endoscopy (Year: 2012).*

NHS, Coronary artery bypass graft, 2020 Link: https://web.archive.org/web/20200329211057/https://www.nhs.uk/conditions/coronary-artery-bypass-graft-cabg/what-happens/ (Year: 2020).*

Pereira et al., "Augmented Reality Microsurgical Planning with a Smartphone (ARM-PS): A dissection route map in your pocket", 2019 (Year: 2019).*

Bengtsson, "Augmented Reality for Safer Coronary Artery Bypass", Jul. 30, 2003 (Year: 2003).*

Valenzuela et al., "Assessment of single and double coronary bifurcation stenting techniques using multimodal imaging and 3D

(56)　　　　　References Cited

OTHER PUBLICATIONS modeling in reanimated swine hearts using Visible Heart® methodologies", May 16, 2021 (Year: 2021).*

Lumdsen et al., "Subcutaneous, video-assisted saphenous vein harvest: report of the first 30 cases", 1996 (Year: 1996).*

Hussaini et al., "Evaluation of endoscopic vein extraction on structural and functional viability of saphenous vein endothelium", 2011 (Year: 2011).*

Wilmot et al., "Categorizing the Distribution of the Saphenous Nerve in Relation to the Great Saphenous Vein", 2013 (Year: 2013).*

2009, Maquet Vasovision Brochure.

* cited by examiner

Sensor Data

85    Matrix    86    Pattern Recognition    Objects    3-D Model    78

Images    Locations

Labels To Display 84    85    88    87
Br    Saph    86

100    101    104    103
Back    Fore    102

112

111

110

116

D=2.2mm

115

130

133

132

131

131

135          136          140          141

OFF
PATH

137

AUGMENTED-REALITY ENDOSCOPIC VESSEL HARVESTING

CROSS REFERENCE TO RELATED APPLICATIONS

Not Applicable.

STATEMENT REGARDING FEDERALLY SPONSORED RESEARCH

Not Applicable.

BACKGROUND OF THE INVENTION

The present invention relates in general to devices and methods for endoscopic dissection of a blood vessel within the limb of a patient, and, more specifically, to integrating an endoscopic vessel harvesting system with an augmented-reality device to improve the ease of use and to improve patient outcomes.

In connection with coronary artery bypass grafting (CABG), a blood vessel or vessel section, such as an artery or vein, is "harvested" (i.e., removed) from its natural location in a patient's body to use it elsewhere in the body. In CABG surgery, for example, the blood vessel is used to form a bypass between an arterial blood source and the coronary artery that is to be bypassed. Among the preferred sources for the vessel to be used as the bypass graft are the saphenous veins in the legs and the radial arteries in the arms.

Endoscopic surgical procedures for subcutaneously harvesting a section of a vein (e.g., the saphenous vein) have been developed in order to avoid disadvantages and potential complications of harvesting through a continuous incision. One such minimally-invasive technique employs a small incision for locating the desired vessel and for introducing one or more endoscopic harvesting devices. Primary dissection occurs by introduction of a dissecting instrument through the incision to create a working space and separate the vessel from the surrounding tissue. Then a cutting instrument is introduced into the working space to sever the blood vessel from the connective tissue and side branches of the blood vessel. The branches may be cauterized using the cutting instrument.

In one typical procedure, the endoscopic entry site is located near the midpoint of the vessel being harvested, with dissection and cutting of branches proceeding in both directions along the vessel from the entry site. In order to remove the desired section of the blood vessel, a second small incision, or stab wound, is made at one end thereof and the blood vessel section is ligated. A third small incision is made at the other end of the blood vessel section which is then ligated, thereby allowing the desired section to be completely removed through the first incision. Alternatively, only the first two incisions may be necessary if the length of the endoscopic device is sufficient to obtain the desired length of the blood vessel while working in only one direction along the vessel from the entry point.

An example of a commercially available product for performing the endoscopic vein harvesting described above is the VirtuoSaph Plus® Endoscopic Vessel Harvesting System from Terumo Cardiovascular Systems Corporation of Ann Arbor, Mich. An endoscopic vessel harvesting system of this type is also shown in U.S. Pat. Nos. 7,331,971 and 8,048,100 and U.S. patent application publications 2010/0292533 and 2012/0035606, which are incorporated herein by reference in their entirety.

The dissector tool typically comprises a longitudinal stainless steel or plastic rod with a tip at one end and an operator handle at the other. The tip is tapered to a blunt end and is made of transparent plastic. The dissection proceeds along the perimeter of the vessel being harvested to separate it from the surrounding tissue and to expose the side branches of the vessel so that they can be severed with the cutting tool. In the VirtuoSaph® Plus® System, the cutting tool for severing and cauterizing branches has the form of a V-cutter wherein a V-shaped tip is extendable from the distal end of the unit to guide a branch to be cut into a longitudinal slit. Electrodes adjacent the slit are electrically energized with a high frequency voltage in order to cauterize and sever the branch by coagulation. A V-keeper also extends from the distal end in order to capture the vessel and to guide the tool along the vessel.

An internal endoscopic view is provided to the user via an optical system having a camera and a video display. The camera can be mounted within the distal tip of the harvesting device. Alternatively, a lens and optical fiber installed in the harvesting device can carry an image to a camera located at a remote end of the optical fiber outside the harvesting device or in the handle of the device. The field of view is illuminated by a light source such as an LED mounted at the tip of the harvesting device (dissector or cutter) or a remote source which inputs light to an optical fiber which runs through the harvesting device to emit light from the tip.

The endoscopic camera view during the dissection or cutting phases is displayed on a computer monitor. Significant training may be required for a user to become skilled in properly coordinating their movements with the dissecting/cutting instruments while looking away from the patient toward the monitor.

SUMMARY OF THE INVENTION

Augmented reality (AR) is an interactive experience of a real-world environment where the objects that reside in the real world are enhanced by computer-generated perceptual information, sometimes across multiple sensory modalities, including visual, auditory, haptic, somatosensory, and olfactory. In particular, an augmented-reality display may include eyewear with an open viewfield for viewing physical objects and an augmented viewing portion configured to render glyphs and/or video content.

In one aspect of the invention, a vessel harvesting system comprises an endoscopic camera of an endoscopic instrument capturing images from a distal tip of the instrument within a dissected tunnel around a vessel to be harvested. An image processor assembles a three-dimensional model of the tunnel from a series of images captured by the endoscopic camera. An augmented-reality display coupled to the image processor renders (e.g., visibly displays to the user in their field of view) a consolidated map representing the three-dimensional model along with a marker in association with the map indicating a current location of the distal tip.

DETAILED DESCRIPTION OF PREFERRED EMBODIMENTS

Figure 1:
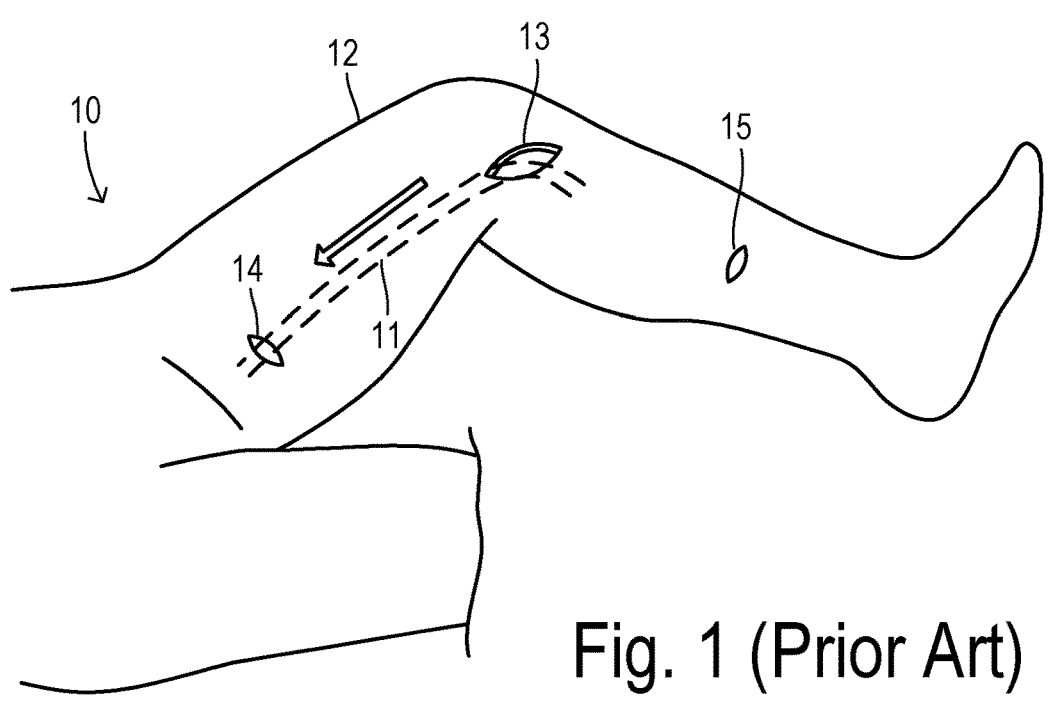
FIG. 1 is an external view of a saphenous vein being harvested from a leg.

Referring to FIG. 1, a patient 10 has a saphenous vein 11 within a lower limb 12. An incision 13 is made directly above vein 11, and tissue is peeled back from incision 13 to access the vein. Endoscopic instruments are inserted through incision 13 to separate vein 11 from connective tissue and then to sever and cauterize side branches that extend from vein 11. A second incision or stab wound 14 is created at a second position on limb 12 so that a second end of vein 11 can be severed. Vein 11 is then extracted through one of the incisions. The entry point and/or second incision or stab wound can be placed at various locations along vein 11 as shown at 15.

Figure 2:
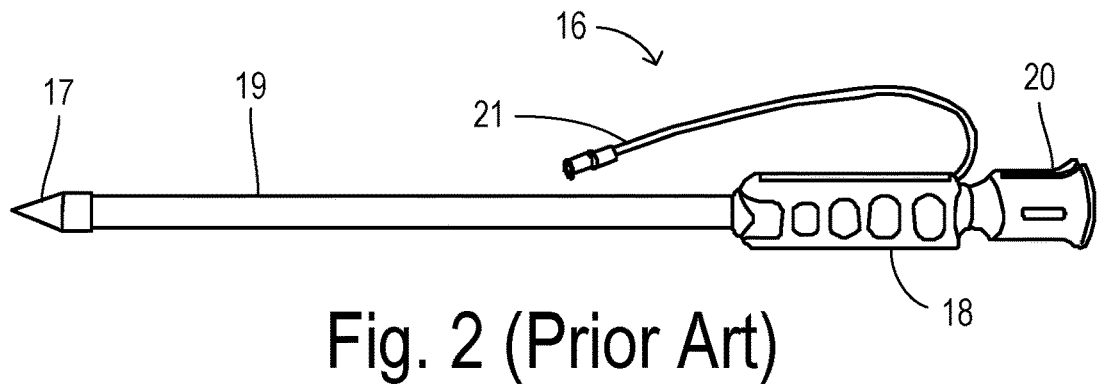
FIG. 2 is a side view of a prior art dissector unit.

A known dissector unit 16 is shown in FIG. 2 for endoscopic dissection of a saphenous vein or other vessel by insertion through an initial incision and then pressing a dissector tip 17 into the fat along the direction of the vessel to separate it from adjacent tissue. Dissector unit 16 has a handle 18 connected to a longitudinal rod 19 having dissector tip 17 at its distal end. A receiver 20 at the end of handle 18 receives an endoscope and optical cable (not shown) for extending through rod 19 to dissector tip 17 which is transparent in order to allow visualization of the vessel and surrounding tissue. An insufflation tube 21 passes through handle 12 and is part of an insufflation gas channel extending to a release hole in or near tip 17. Tube 21 is connected to a source of $CO_2$ or other insufflation gas for filling the cavity adjacent the vessel as it is being formed.

Figure 3:
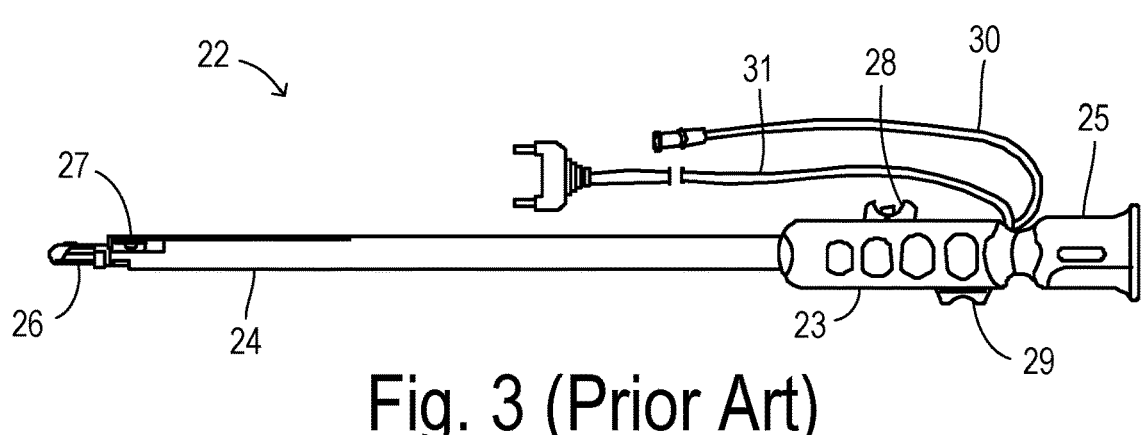
FIG. 3 is a side view of a prior art cutting unit.

After initial blunt dissection around the vessel, a harvester cutting unit 22 as shown in FIG. 3 is used subcutaneously to grasp the vessel being dissected and to sever any branches or connective tissue connecting to the vessel. Harvester 22 has a handle 23 connected to an elongated sleeve member 24 and an endoscope receiver 25. At the distal end of sleeve 24 are a vessel keeper (V-keeper) 26 for retaining the vessel being dissected and a vessel cutter (V-cutter) 27 for severing branches. V-keeper 26 is manipulated by V-keeper buttons 28 on handle 23. V-cutter 27 is extended or retracted by manipulating a V-cutter extender button 29 on handle 23. An insufflator tube 30 is adapted to be connected to an insufflation source to deliver the gas to the distal end of sleeve 24 via a gas channel extending between handle 23 at the proximal end and a release hole at the distal end. A bipolar or integrated bipolar cord 31 connects to a source of high frequency voltage, and includes conductors for supplying the voltage to electrodes on V-cutter 27 for cutting and cauterizing the branches and connective tissue.

In some embodiments, cutting and cauterizing may be accomplished using a pair of scissor-like jaws instead of a V-cutter. The jaws may have electrodes or other energizable devices on inner surfaces that are clamped onto a side branch for being cut.

Figure 4:
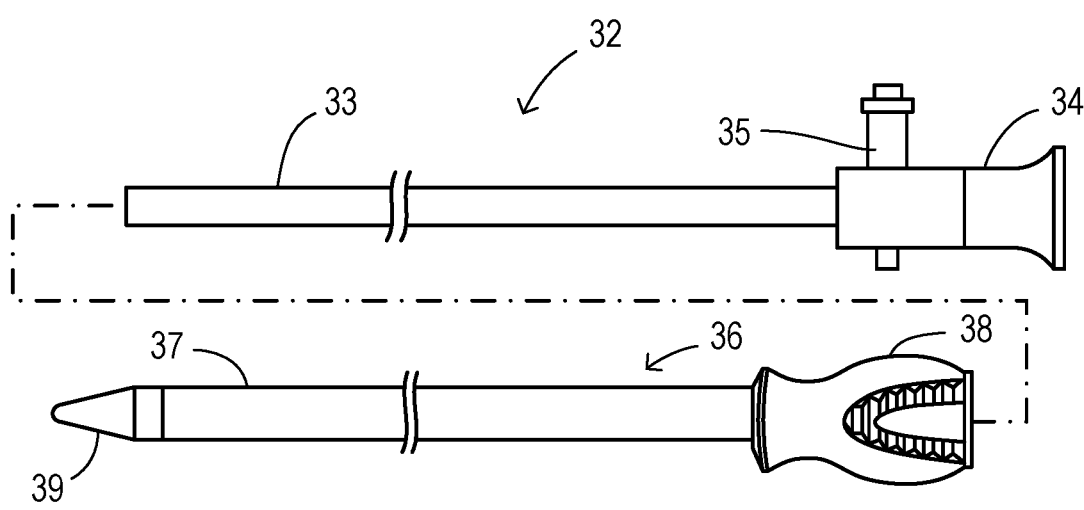
FIG. 4 is a plan view of a prior art blunt dissector with an endoscope and a trocar.
Figure 5:
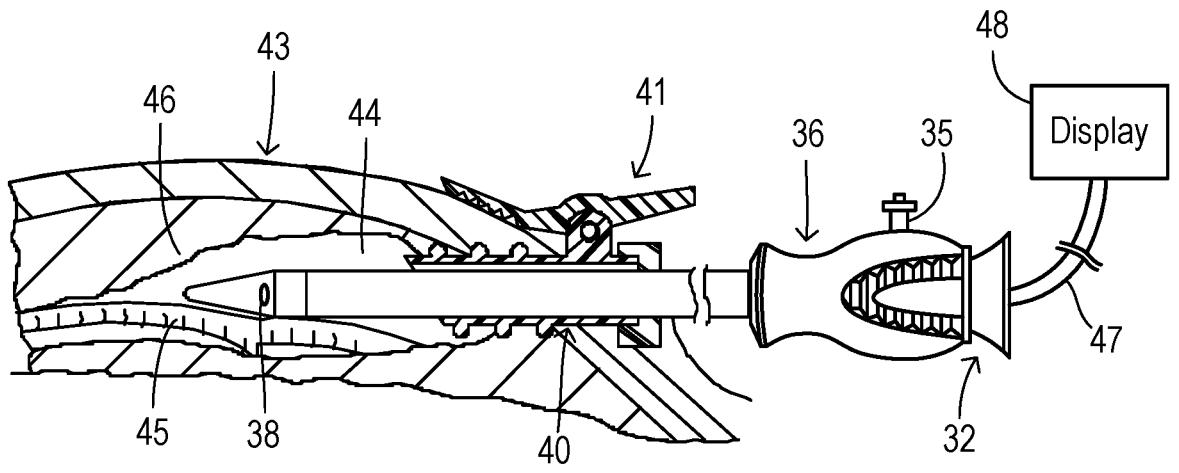
FIG. 5 is a partial cross-sectional view of the dissection of a blood vessel.

FIGS. 4 and 5 show another vessel harvesting system which includes an endoscope unit 32 to perform observation in a patient's body, a dissector unit 36 to dissect a blood vessel in the body, and a trocar 40 to help insert the endoscope 32 and dissector unit 36 into the body. An optical system is shown as a rigid endoscope 32 which has an elongated rod-like inserting portion 33. The proximal end of inserting portion 33 connects to an end adapter 34 to transmit an endoscopic image. A light guide port 35 projects from end adapter 34 to connect to a light guide cable which supplies illumination light to endoscope 32. In other embodiments, the optical system can employ a camera and LED light source installed at the distal end of endoscope 32 connected via electrical cables to power and a video image processor.

Dissector unit 36 has a tubular main body portion comprising a hollow longitudinal rod 37 within which endoscope 32 is to be inserted. Endoscope 32 is inserted or removed from longitudinal rod 37 through a handle portion 38. The material of longitudinal rod 37 may be comprised of fluoropolymers. The most preferred material for constituting the outer surface of longitudinal rod 37 is polytetrafluoroethylene (PTFE). The use of a fluoropolymer reduces the friction caused by moving rod 37 through connective tissue, thereby reducing the force required to perform a dissection.

A blunt dissector tip 39 is disposed at the distal end of longitudinal rod 37. Tip 39 has a conical shape and comprises a transparent synthetic resin material to facilitate viewing through tip 39 using endoscope 32. Trocar 40 guides dissector unit 36 into the incision site. An outer surface of trocar 40 includes a projection to engage with living tissue and a holding portion 41 to hold trocar 40 onto the living tissue 43 (e.g., patient's skin). Since the inserting direction of dissector 36 is along the direction of a target blood vessel 45 being dissected, the operator gradually inserts the dissector so as to dissect peripheral tissue 46 from blood vessel 45 (creating a working tunnel 44) while viewing the endoscope image on a display 48 which is connected to endoscope 32 by cables 47.

Figure 6:
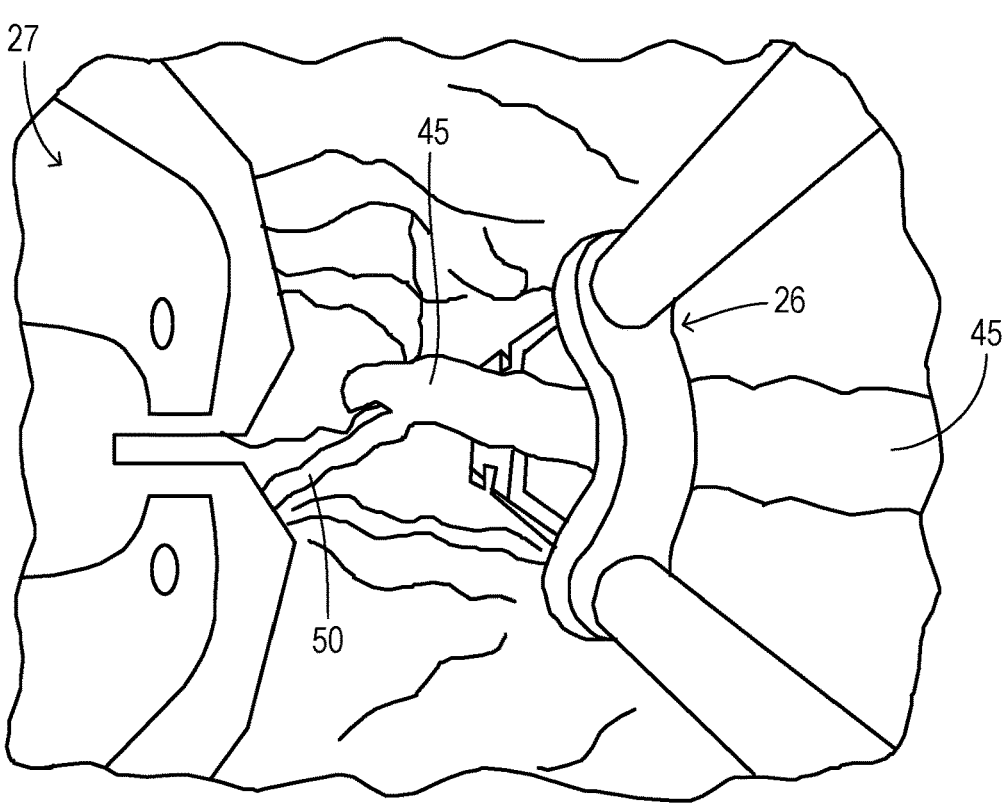
FIG. 6 is an endoscopic camera view depicting a V-keeper and a V-cutter of the harvester unit deployed within a working tunnel around a target vessel.

After dissecting a working tunnel along the target vessel, a dissector instrument may be removed and a cutting instrument may be inserted into the working tunnel to sever the target vessel from any side branches and from any connective tissue that has not been dissected. FIG. 6 shows an endoscopic view as seen during vessel harvesting wherein a target vessel 45 (e.g., saphenous vein) is retained within V-keeper 26. A side branch 50 extends from vessel 45 within the tunnel created previously during blunt dissection. V-cutter 27 is in position for extending toward side branch 50 for cauterizing and severing it to prepare a section of vessel 45 for removal. Since side branches such as side branch 50 extend in various radial directions away from vessel 45, the harvester must be rotated around vessel 45 to directly approach all the different side branches along the length of vessel 45 being harvested. For many reasons, it may be challenging for a user to maintain a good mental picture of the subcutaneous structures and where within that mental picture the instrument head is located as they monitor their progress looking at a computer monitor.

Figure 7:
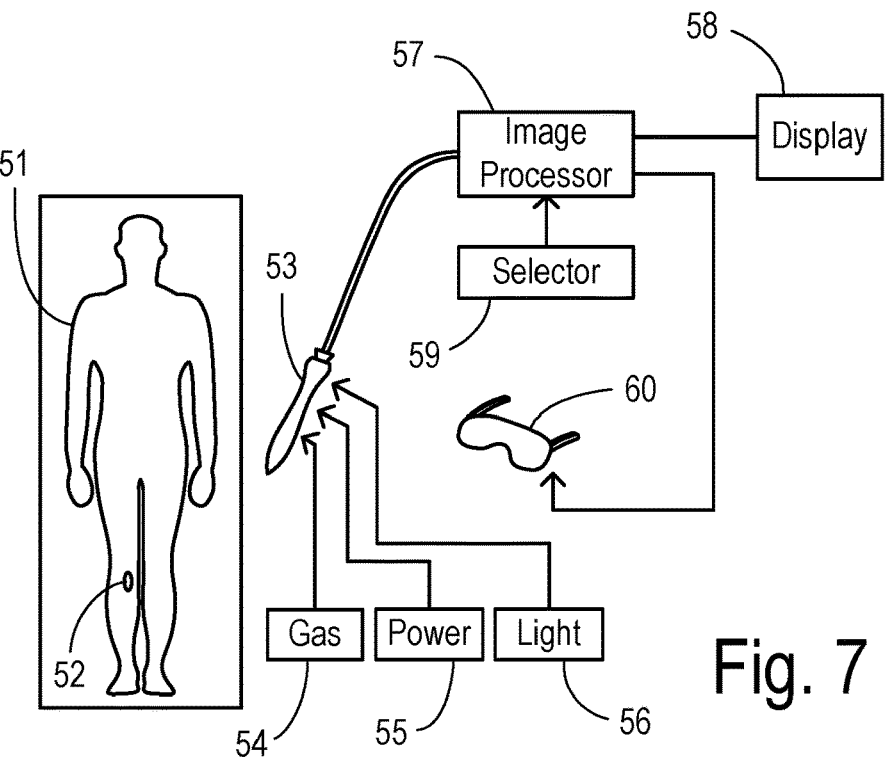
FIG. 7 is a block diagram showing one embodiment of a vessel harvesting system with augmented reality.

FIG. 7 shows a first embodiment of a vessel harvesting system using augmented reality to assist a user in maintaining their bearings as they work on dissection and cutting phases. A patient 51 has an incision 52 where a harvesting instrument (e.g., dissector or cutter) 53 is inserted. Instrument 53 is coupled to a source of insufflation gas 54, a power source 55, and a light source 56. Camera images from instrument 53 are coupled to an image processor 57, and processed images may be coupled to a conventional display 58 and/or an augmented-reality display 60. A selector 59 is coupled to image processor 57 which can be utilized by a user to initiate commands which update augmented reality contents of display 60. Preferably, selector 59 is configured to generate commands in a hands-free manner as described below.

Augmented-reality display 60 may be comprised of a head-worn display, sometimes also referred to as "smart glass" or "smart glasses", among other names. For example, display 60 can take the form of a pair of glasses, a visor, an open area, or a face-shield that a user (e.g., a surgical technician or physician's assistant) wears on their head or face. Display 60 includes a viewfield through which a user can view physical objects in their field of view, which is sometimes referred to as "non-occluded" or "non-occluded heads-up display (HUD)", among other names. For example, there may be a clear portion of glass, plastic, or similar transparent material through which light emitted from physical objects passes into the user's eye. In some embodiments, display 60 may include solid or opaque portions that completely or partially occludes the user's view, sometimes referred to as "occluded" or an "occluded HUD", among other names. The viewfield can include one or more screens (e.g., Light Emitting Diode or LED screens) along with one or more cameras that capture a video data of the user's point-of-view. Video is then rendered on the screens, providing the user with a viewfield that is similar to a clear view of the physical environment.

In another example, display 60 can include a retinal projector configured to project an image directly onto the wearer's eye or eyes. In some cases, the retinal projector can include a clear portion of glass, plastic, or similar transparent material through which light emitted from physical objects passes into the user's eye. In some cases, a display 60 with retinal projector can include one or more cameras that capture a video data of the user's point-of-view. Video is then rendered and projected onto the user's eye, or eyes, providing the user with a viewfield that is similar to a clear view of the physical environment. In some implementations, display 60 can be configured to account for seeing difficulties of the user. For example, a retinal projector can be configured to provide a projection to a user with a cloudy cornea or cataracts in a way that is clear to such a user.

In yet another example, display 60 can include a half-mirrored portion of glass, plastic, or similar transparent material through which light emitted from physical objects passes into the user's eye, while light is emitted onto the half-mirror view field to render glyphs etc.

Augmented-reality display 60 is configured to render glyphs (e.g., text, symbols, colored overlays, etc.) and to render video in the viewfield. For example, light emitters can emit light into a transparent viewfield so that the user is shown a reflection of the light. In another example, where screens are used to show video from the user's point-of-view, the glyphs and video can be shown superimposed over the point-of-view video. In any case, display 60 shows a presentation of the glyphs and the video as an overlay to the view of the physical objects.

Display 60 can include other features as well. For example, a microphone and earphone may be included for connecting to an intercom, cellular phone, or other telecommunication device. This can allow the operator to communicate, via the microphone and earphone, with people in the same facility or more distant.

As discussed in more detail below, many different types of glyphs and video images can be displayed to the user. Selector 59 enables the user to generate a screen update command in order to modify the contents of display 60 (e.g., selecting different glyphs, scrolling through monitored physiologic parameters of the patient, selecting different image sources, or altering characteristics of the displayed items such as zooming in on a region of the images). Since it is desirable for the user (e.g., wearer of display 60) to maintain their hand grip on the harvesting instrument, selector 59 is configured to receive commands while the user continues to hold the instrument. Selector 59 may be comprised of a manual control mounted on the instrument in its gripping area. Otherwise, selector 59 may be comprised of a hands-free device which senses other actions by the user. For example, selector 59 may include an eye-tracking camera which detects specified eye movements of the user which have been designated to trigger a corresponding update command. Alternatively, selector 59 may include either 1) a microphone and a voice recognition system so that the user can generate the screen update command as a spoken command, 2) a motion sensor responsive to predetermined movements of the user, or 3) a foot pedal (e.g., coupled to image processor 57 via a Bluetooth® connection) with one or more switches to generate a desired update command.

Figure 8:
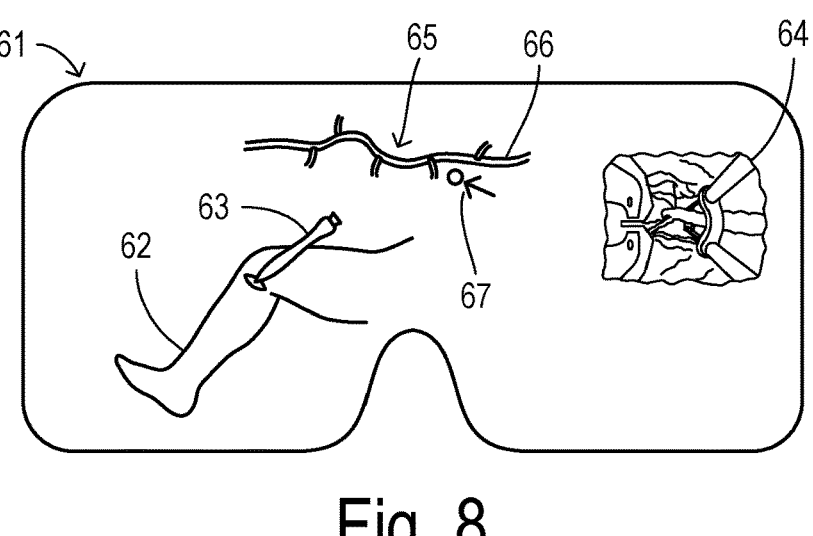
FIG. 8 is a schematic diagram showing an augmented-reality presentation which renders a three-dimensional model of a tunnel/vessel during harvesting.

FIG. 8 shows an example of a viewfield 61 on and through the augmented-reality display. A transparent portion of viewfield 61 with no overlays provides a real, live view of a patient's limb 62 and an endoscopic instrument 63. An overlay 64 provides a copy of the instantaneous endoscopic image being received by the image processor from the endoscopic camera (e.g., displayed toward a lateral side of the viewfield). An overlay 65 (e.g., displayed toward an upper side of the viewfield) renders a consolidated map representing a three-dimensional model of the surgical anatomy (e.g., the target vessel, its side branches, and other aspects of the dissected tunnel) and a marker which is placed in association with the 3-D map to indicate a current location of the distal tip of the endoscopic instrument head relative to the 3-D map.

In some embodiments, an image processor (e.g., a local or a remote computer-based unit in communication with the endoscopic instrument and which performs at least a portion of an image processing task using images captured by the endoscopic camera) assembles a three-dimensional model of the tunnel a vessel structures from a series of images captured over time by the endoscopic camera. The image processor may be configured for feature point extraction using a comparison of changing positions of detected features within the series of images to determine estimated distances between the detected features within the three-dimensional model. A process for assembling a 3-D model may include an automated stitching together of image data from overlapping and/or adjacent viewfields as is done for creating panorama types of images.

Figure 9:
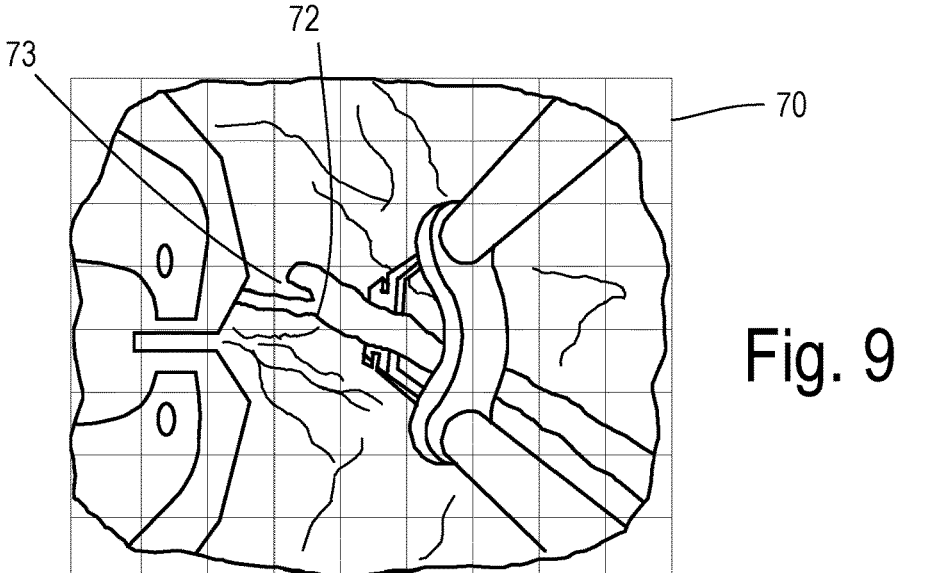
FIGS. 9 and 10 show endoscopic camera views with shifting features as a cutting tool advances along a dissected tunnel.
Figure 10:
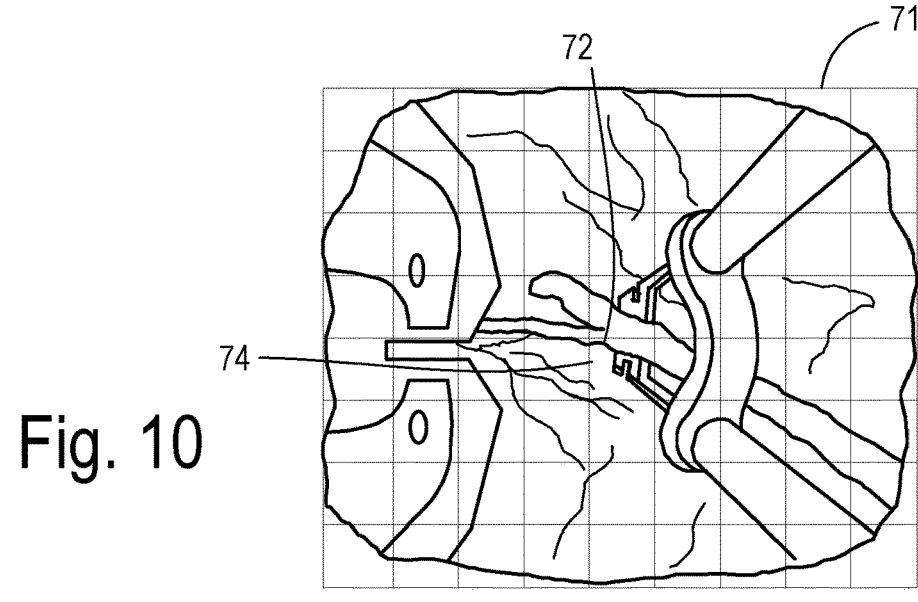

FIG. 9 shows a first captured image taken at a particular position along the dissection tunnel. Images may contain one or more recognizable features that are suitable for tracking in order to establish points of reference along the tunnel, such as side branches, distinctively shaped sections of connective tissue, pockets of fatty tissue, or other optically stable markings. As the endoscopic instrument head progresses along the tunnel, apparent positions of the trackable features will shift. FIGS. 9 and 10 show imaginary grids 70 and 71 which remain fixed with respect to the endoscopic camera, so that as the imaging position changes then the trackable features move with respect to grids 70 and 71. For example, a feature 72 corresponds to a branching point where a particular side branch joins with a main target vessel. In FIG. 9, feature 72 appears in a grid square 73. An endoscopic camera view in FIG. 10 corresponds to a camera position which has been advanced along the tunnel, resulting in feature 72 appearing in a different grid square 74. The image processing estimates relative distances between various trackable features in order to compile a 3-D model of the tunnel and structures within the tunnel. Based on the model, a projection can be determined in order to create a meaningful representation (e.g., map) to simulate the appearance of the tunnel/vessel to the user on an augmented reality overlay.

Figure 11:
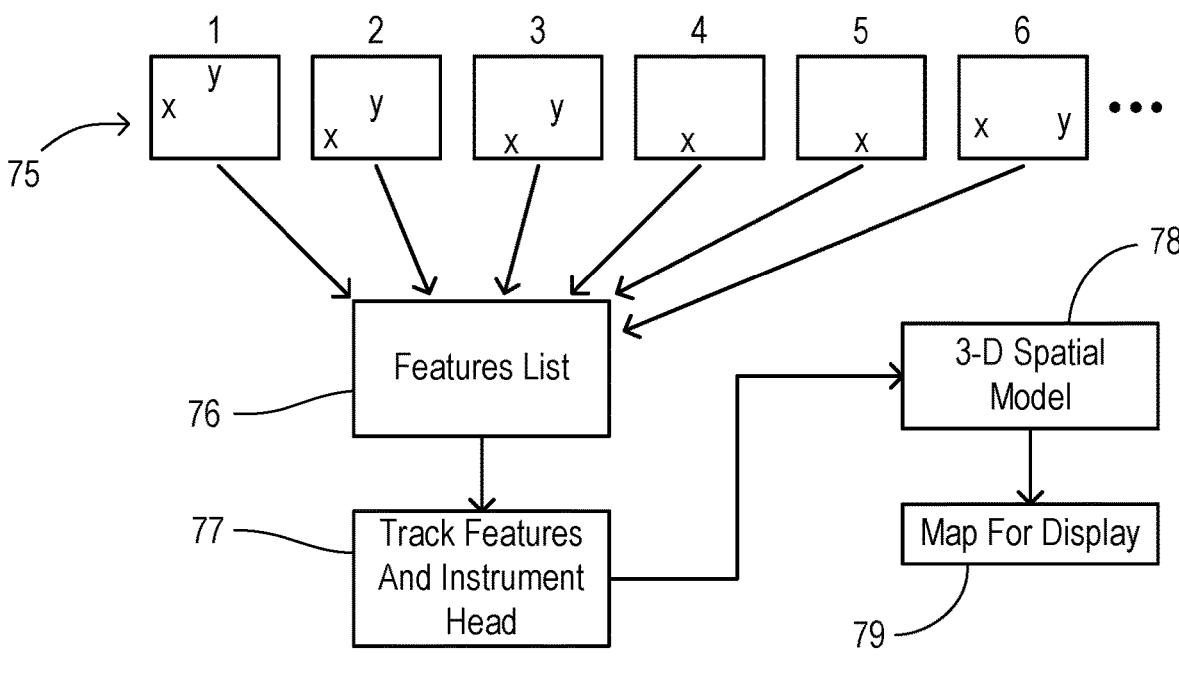
FIG. 11 is a block diagram showing components for compiling a three-dimensional model and generating a map for rendering on the augmented-reality display.

FIG. 11 provides a diagram showing a process for compiling a 3-D model and a projected map image. Images 1 through 6 of a series of images 75 are shown with the changing positions of a pair of features shown as x and y. Features x and y drift in position from one image to the next. As features are identified, they are added to a features list 76. Locations of the listed features (e.g., as compared to a location of the instrument head or distal tip) are tracked and stored in a tracking list 77. By linking up the changing positions of a multitude of different features as more and more images are captured along the tunnel (e.g., as the tunnel is created by dissection or while the tunnel is traversed for subsequent cutting activity), a fuller picture of the size and shape of the tunnel and structures is recorded. The linking of the features and estimates of relative distances results in a 3-D spatial model 78 which mathematically defines three-dimensional surfaces in the tunnel. For display on the augmented-reality display, a simulated exterior view of the 3-D spatial model is generated as a map 79. The map may include a projection of the vessel and side branches extending from the vessel from a perspective as would be seen from the location of the augmented-reality display, for example.

Figure 12:
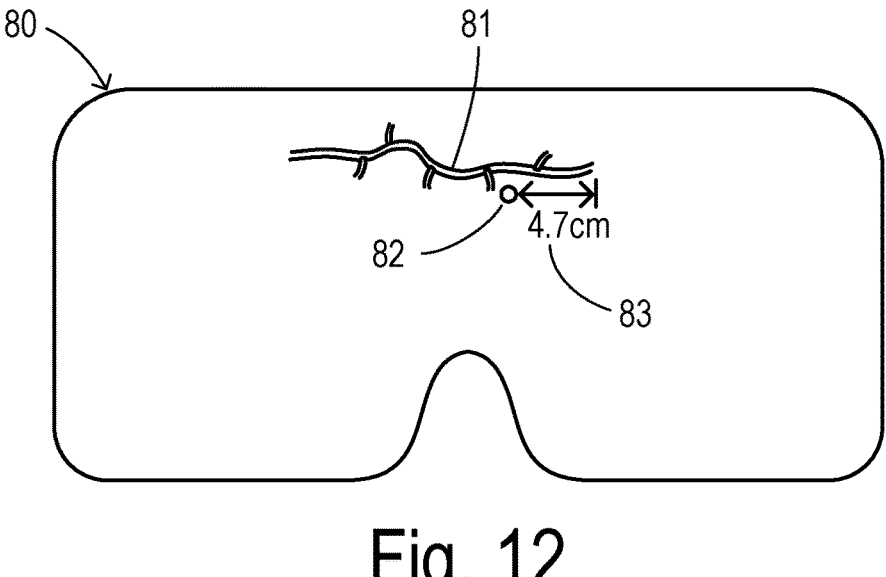
FIG. 12 is a schematic diagram showing an augmented-reality presentation rendering an actual size indicator.

FIG. 12 shows an example viewfield 80 with 1) a map overlay 81 which renders a map projection of the 3-D model of the target vessel, and 2) a marker 82 which indicates a current location of the distal tip end of the endoscopic vessel harvesting instrument head. In addition, an actual size/distance marker 83 is overlaid on viewfield 80 in association with may overlay 81 to indicate a corresponding length of a portion of the 3-D model. For example, marker 83 is a textual glyph which provides a length estimate of the distance from the cutaneous entry incision (e.g., the starting point of the dissection) to the current instrument location at marker 82.

Figures 13, 14, 16:
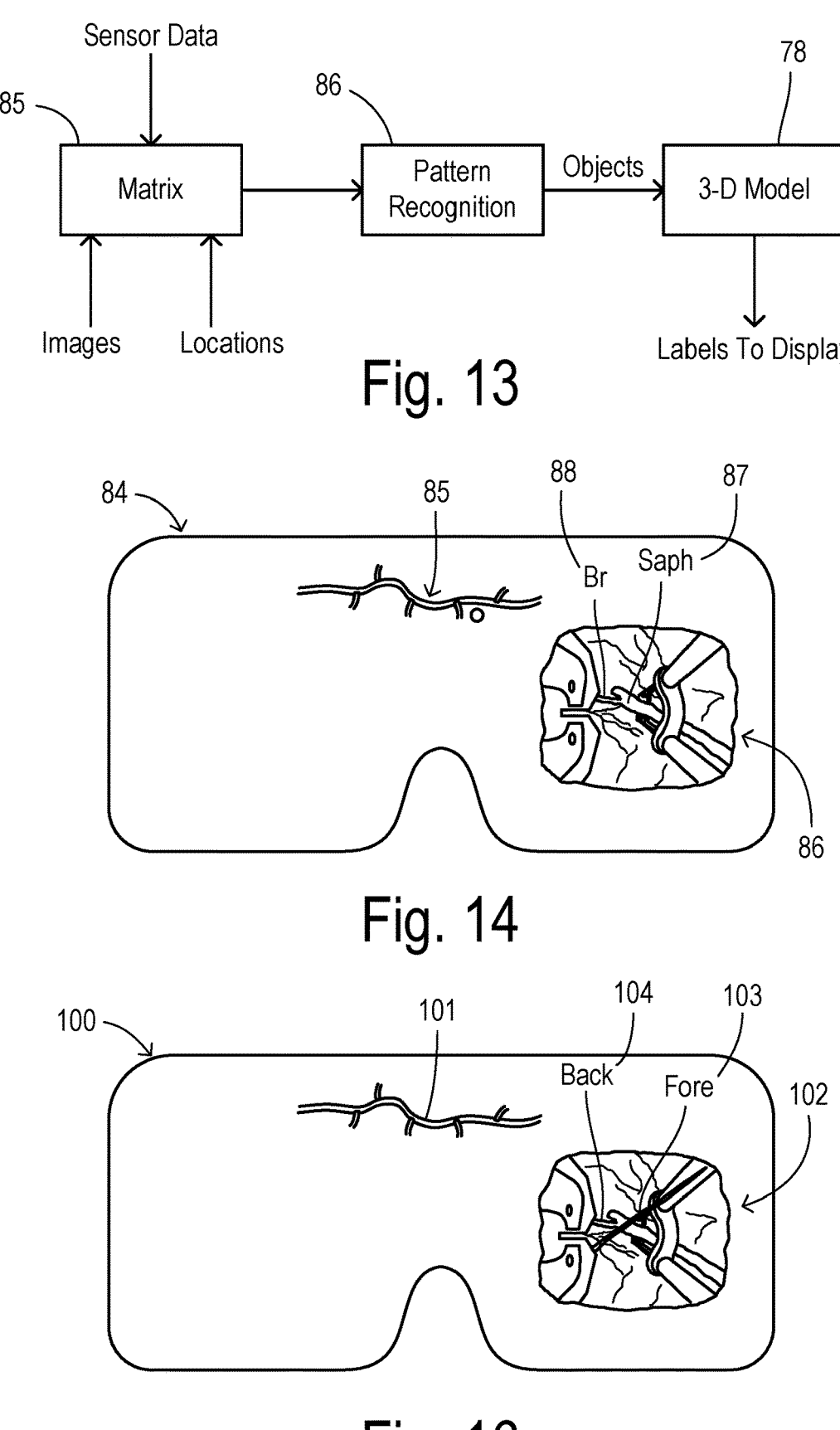
FIG. 13 is a block diagram showing components for identifying a type of structure seen in the endoscopic camera image.
FIG. 14 is a schematic diagram showing an augmented-reality presentation rendering a structure identification indicator.
FIG. 16 is a schematic diagram showing an augmented-reality presentation rendering a relative depth indicator.

In some embodiments, a user can be assisted in identifying particular anatomical objects (e.g., specific vessels, side branches, or connective tissue) based on pattern recognition. As shown in FIG. 13, a matrix 85 stores the series of captured images along with estimated locations of the camera from which each image was captured and/or the estimated locations of detected features. Matrix 85 may also compile other sensor data (such as ranging information or effects relating to blood flow such as fractional flow reserve (FFR) or speckle interference) to assist in object recognition. Data from matrix 85 is applied to a pattern recognition engine 86 which output the identities and locations of classified object to 3-D model 78. For detected objects which have been classified and which are visible in a current endoscopic camera view, corresponding labels are generated and/or relayed by 3-D model 78 to be presented as glyphs on the augmented-reality display in association with the visible, classified object(s). For example, FIG. 14 shows a viewfield 84 with a map overlay 85 which renders a map projection of the 3-D model of the target vessel and an instantaneous endoscopic camera image 86. Overlaid on viewfield 84 are a structure identification indicator 87 (which indicates a saphenous vein) and a structure identification indicator 88 (which indicates a side branch) which may be comprised of textual glyphs along with lead lines or arrows which point out the specific structure being referenced in the image.

Figure 15:
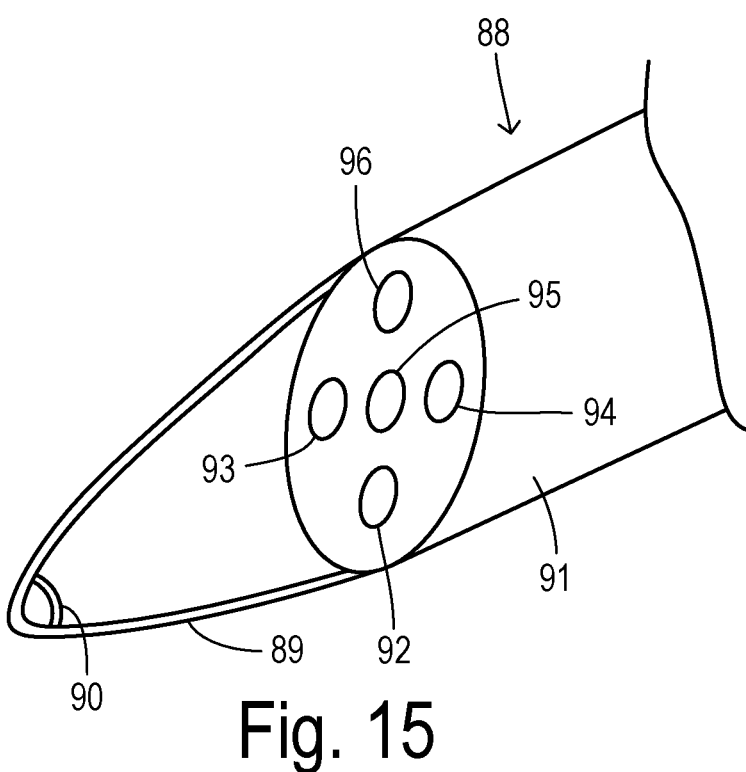
FIG. 15 is a perspective view of a distal tip of a dissector instrument having sensors for detecting depth of structures seen in the endoscopic camera image.

In some embodiments, a depth of visible structures or objects (e.g., a distance from the distal tip of the endoscopic instrument to the object) is included as an overlay. Depth can be estimated or measured. For measuring depth, a ranging sensor can be provided at the distal tip of the endoscopic instrument. FIG. 15 shows a dissector unit 88 with a transparent blunt tip 89 having a cone shape for forming a tunnel by separating a target vessel from surrounding tissues. A discontinuity 90 such as a groove or ledge on an inner surface of tip 89 creates a visible circle around the end of tip 89 as viewed in the endoscopic images in order for the user to track the position of the most distal end of tip 89. A rod portion 91 of dissector 88 carries one or more ranging sensors such as a time-of-flight (TOF) sensor 92. Depth can also be sensed using a stereoscopic imager with images sensors 93 and 94 which are spaced apart along a transverse direction to obtain stereoscopic images from which a depth can be inferred. An active sensor 95, such as a LIDAR, laser, or radar sensor, can also be used to measure the ranges to identified objects or surfaces. A light source 96, such as an LED, is provided at the end of rod portion 91 to provide illumination for obtaining endoscopic images.

Figure 17:
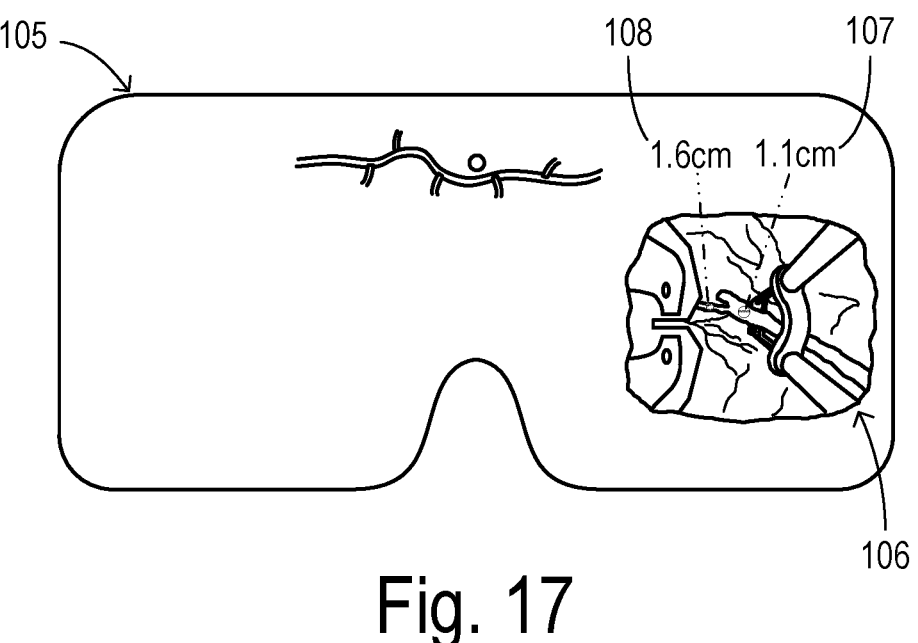
FIG. 17 is a schematic diagram showing an augmented-reality presentation rendering actual size indicators for recognized features.

Using the depth information, overlays can be created to assist a user in approaching and treating target tissues (e.g., connective tissue and side branches). FIG. 16 shows a viewfield 100 with a map overlay 101 which renders a map projection of the 3-D model of the target vessel and an endoscopic video image 102. Video image 102 is enhanced by rendering a foreground overlay 103 and a background overlay 104 which highlight a pair of visible objects or surfaces and indicate a relative depth relationship between the visible structures. The two visible structures may be automatically selected by the image processor based on pattern recognition of significant objects (e.g., a side branch), or a user may specify two points in the video image for evaluation. As shown in FIG. 17, a depth indicator can be provided in order to indicate an actual estimated distance from the distal end of the endoscopic camera lens to at least one visible structure in the instantaneous endoscopic image. Thus, a viewfield 105 includes an endoscopic video image 106 with a depth overlay 107 (indicating a distance of 1.1 cm to an indicated spot on a target vessel) and a depth overlay 108 (indicating a distance of 1.6 cm to a side branch).

Figure 18:
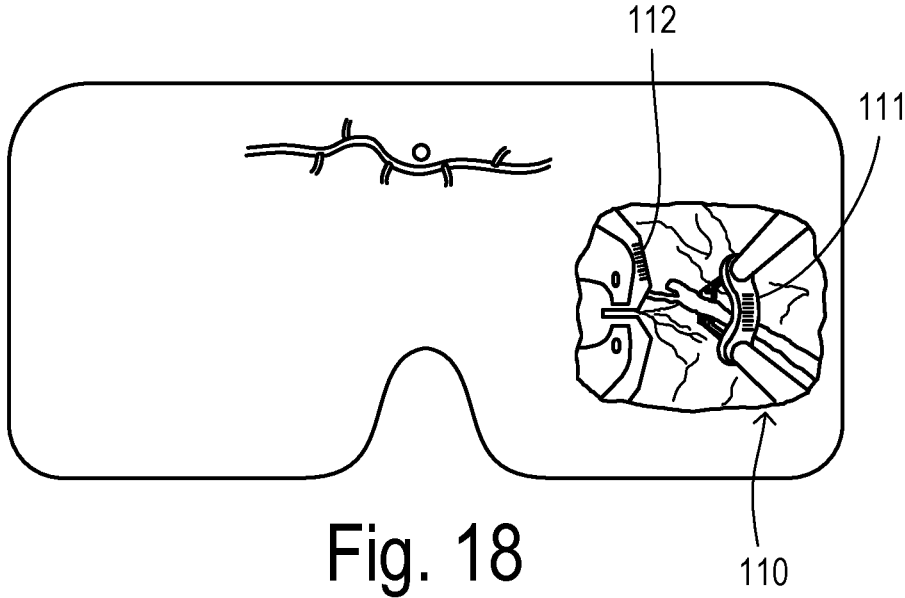
FIG. 18 is a schematic diagram showing an augmented-reality presentation including an image of an endoscopic instrument having size markings.

To further assist a user in understanding the spatial arrangement and sizes of various features in an endoscopic image, a harvesting instrument of the present invention may include absolute reference markings that can be visualized by the user via the endoscopic camera view. FIG. 18 shows an endoscopic video image 110 rendered on the augmented-reality display, wherein the endoscopic instrument (e.g., a V-cutter) has visible surfaces inscribed with linear distance measurement scales. A series of tic marks 111 is provided on a vessel-keeping portion, and a series of tic marks 112 is provided on a cutter/electrode portion. Tic marks 111 and 112 follow any convenient distance progression, which is identified to the user. Tic marks 111 and 112 can be compared visually by the user with nearby structures in the endoscopic video image so that the user can estimate sizes of any features in the image.

Figure 19:
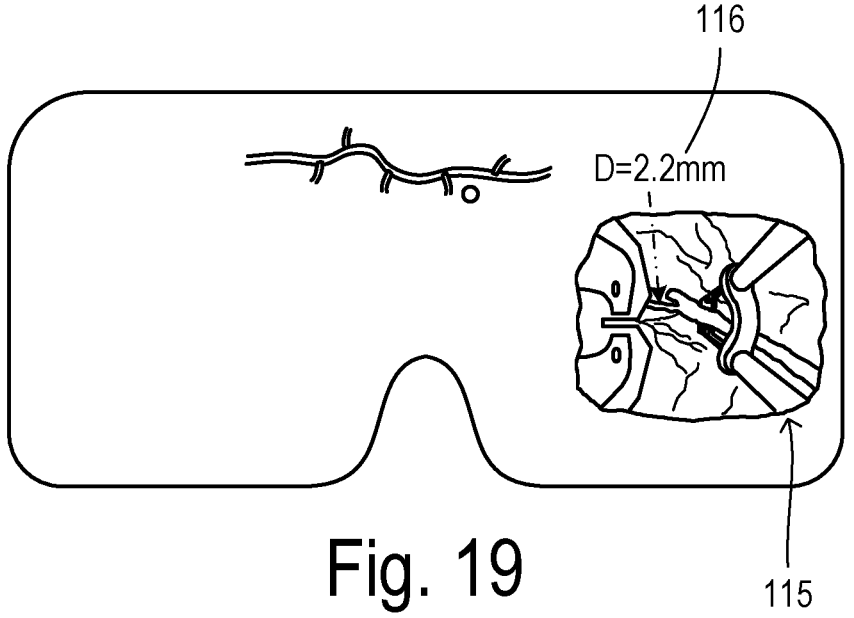
FIG. 19 is a schematic diagram showing an augmented-reality presentation rendering a width indicator for a side branch.

Depth information also facilitates automated determination of the sizes of selected (and/or automatically recognized) structures in an image. As shown in FIG. 19, an instantaneous endoscopic video image 115 rendered on an augmented-reality display can be enhanced with an actual size indicator 116. It may be particularly helpful to a user to know a diameter of a side branch, so that an appropriate amount of cutting/cauterizing energy can be applied to the side branch. Actual size indicator 116 is associated with a side branch which is identified by a pointer. A textual legend indicates a diameter measurement ("D") and an actual diameter distance (e.g., "2.2 mm") which can be automatically estimated by the image processor based on a measured depth from i) the endoscopic lens and ii) the apparent size in the endoscopic image.

In some embodiments, a pre-mapping representation of the target vessel to be harvested is obtained prior to dissecting the endoscopic tunnel. The pre-mapping representation can be used in assembling the three-dimensional model and/or guiding a dissector during the tunnel dissection. The pre-mapping representation can is obtained by transcutaneous sensing of the location of the target vessel. The transcutaneous sensing can be comprised of ultrasonic imaging. The pre-mapping representation can be used to define a dissection path. During dissection, the image processor can compare a current location of the distal tip with the dissection path. Whenever a deviation between the current location of the distal tip and the dissection path exceeds a predetermined threshold, then the augmented-reality display can render a warning to a user. A sound or other warning can also be generated. The warning rendered on the display may also include an instruction for correcting the deviation.

Figure 20:
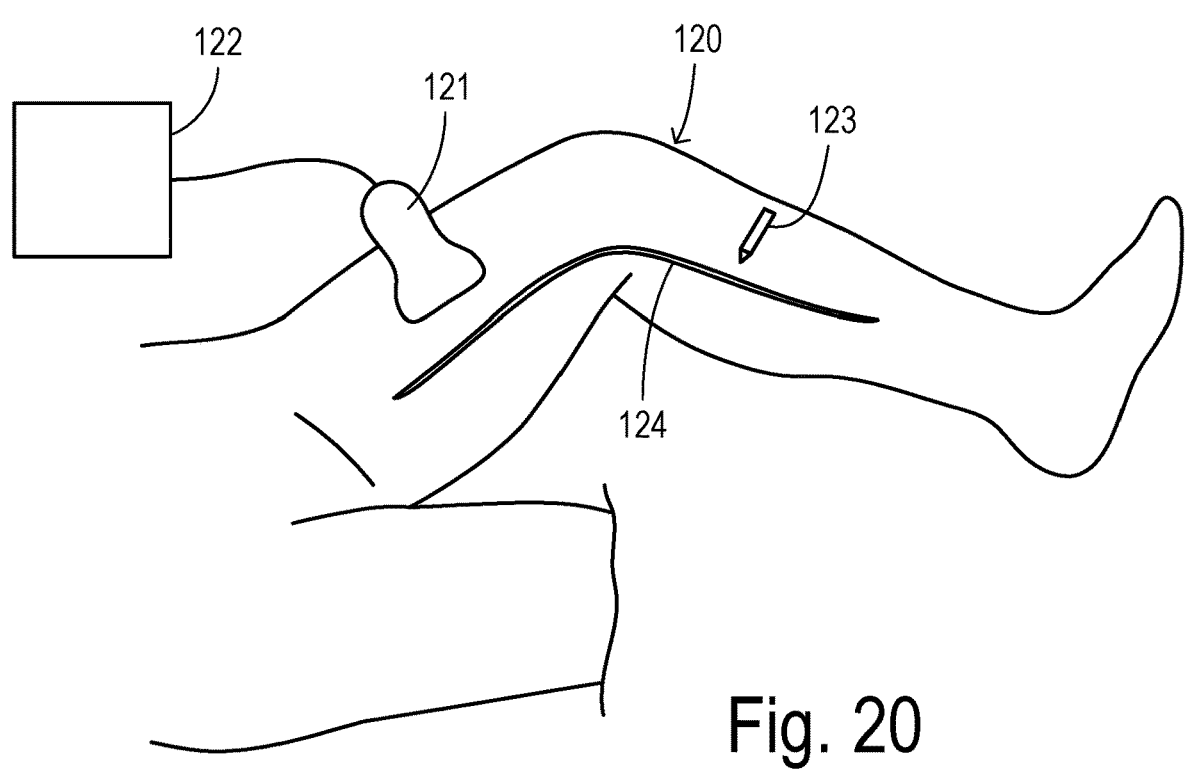
FIG. 20 depicts a pre-mapping of a vessel location onto the skin of a patient.

FIG. 20 shows a patient's lower limb 120 being inspected using an ultrasonic probe 121 coupled to an ultrasound controller/display 122. A user probes limb 120 to identify a target vessel (e.g., a saphenous vein). A marker 123 is used to draw a trace 124 on the skin of limb 120 following the path of the target vessel as is it being detected ultrasonically. Ultrasound controller 122 could be electrically coupled to a processor of the vessel harvesting system in order to provide data characterizing the location(s) of the target vessel, to be used by the vessel harvesting system to generate the 3-D model.

Figure 21:
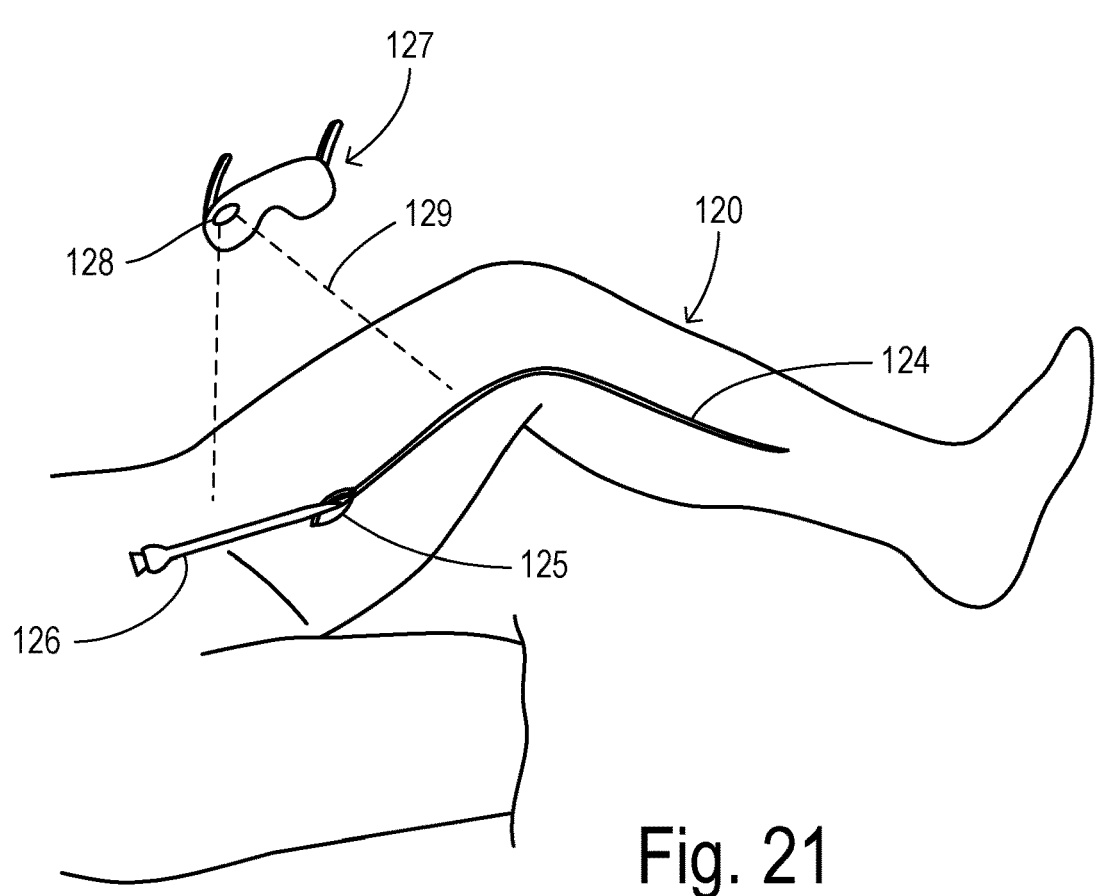
FIG. 21 depicts tracking of a position of an endoscopic instrument relative to a pre-mapped vessel path.
Figure 22:
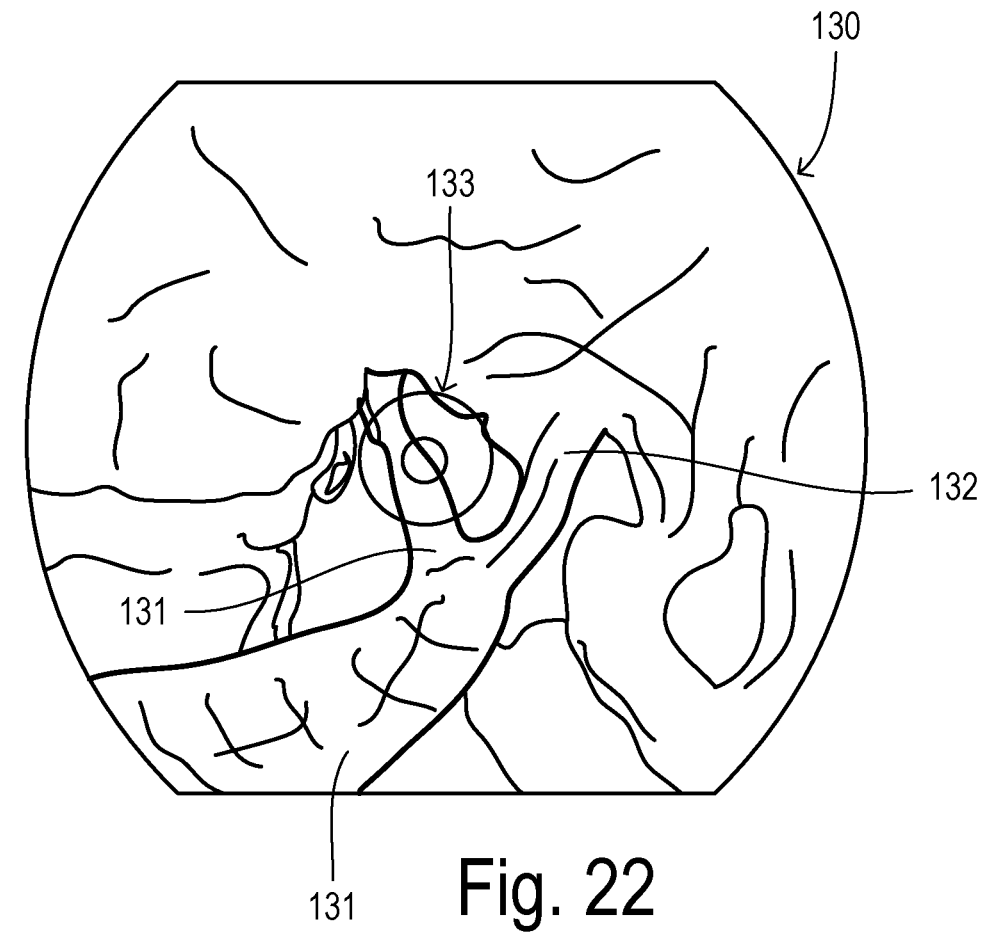
FIG. 22 is an endoscopic camera view seen through a dissector instrument.
Figure 23:
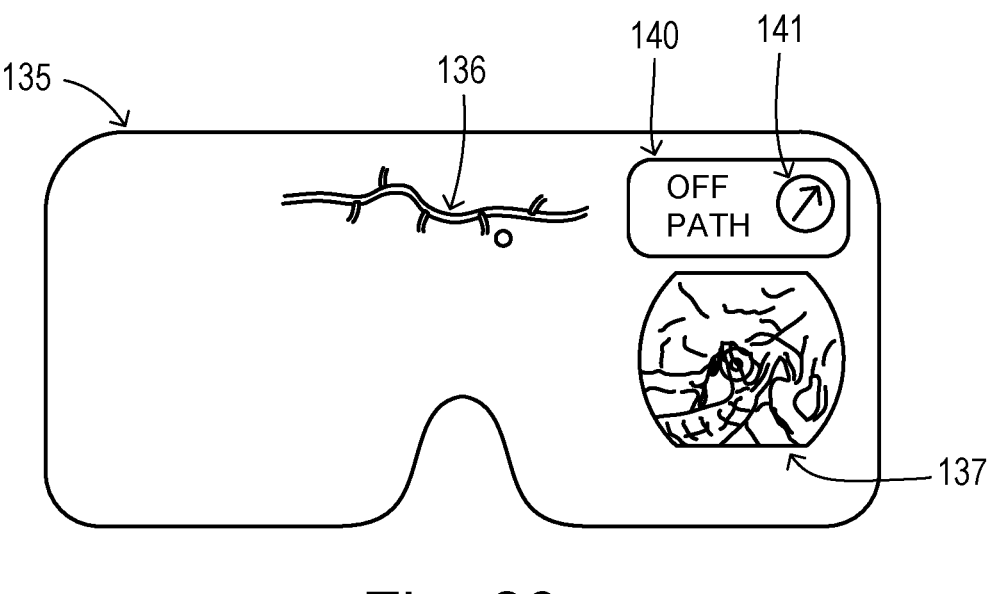
FIG. 23 is a schematic diagram showing an augmented-reality presentation rendering a message generated when the dissecting of a tunnel fails to correspond to the pre-mapped path.

The pre-mapping representation can be used to guide a dissection as shown in FIG. 21. An incision 125 is made to insert a distal tip of a dissecting instrument or dissector 126. A user wears an augmented-reality display 127 which carries a video camera 128 arranged to capture images including lower limb 120, trace 124, and dissector 126. Captured images are transmitted to an image processor/controller (not shown) which is programmed to estimate a subcutaneous location of the distal tip of dissector 126, using an orientation of dissector 126 in the images and by calculating a proportion of the length of dissector 126 which has passed into incision 125 compared to the full length of dissector 126. FIG. 22 shows an example endoscopic view 130 during dissection of a tunnel around a target vessel 131 which has a side branch 132. The dissector has a transparent tip including markings or discontinuities in the inner surface shape of the transparent tip which creates "bulls-eye" markings 133 in the images. FIG. 23 shows a viewfield 135 of an augmented-reality display during a dissection showing a 3-D map projection overlay 136 and an endoscopic camera view 137. As movement of the distal tip of the dissector is tracked, whenever a direction or travel of the dissector diverges from the path of the target vessel, then a warning overlay 140 is generated. Overlay 140 may indicate that the direction of dissection has gone off of the desired path. Based on a direction of the discrepancy, a correction icon 141 can be included in overly 140 to inform the user of the direction that should be taken to reduce the discrepancy.

Figure 24:
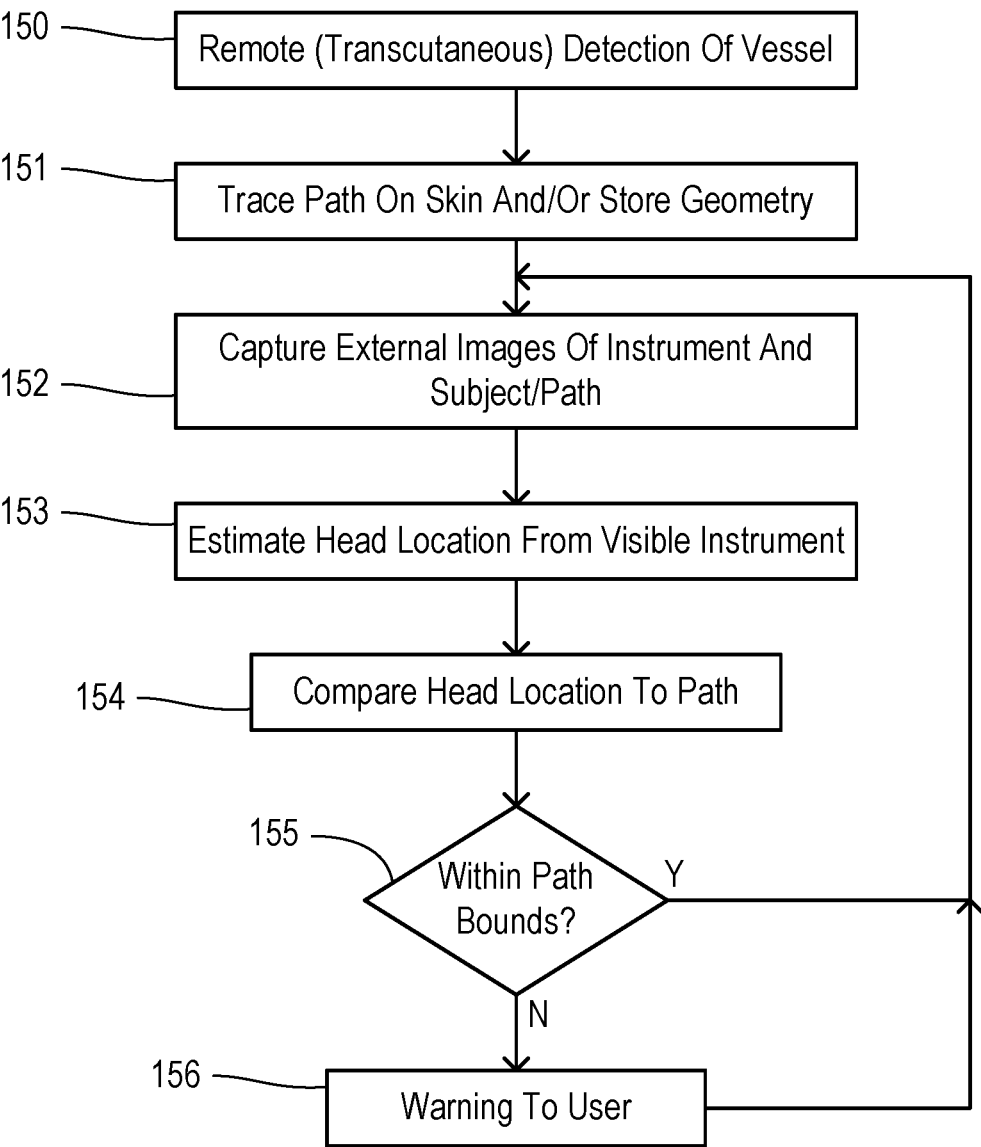
FIG. 24 is a flowchart showing a method of dissecting a tunnel using augmented reality.

FIG. 24 shows a method of the invention wherein a pre-mapping of a path of the target vessel is obtained using remote sensing (e.g., transcutaneous sensing, such as ultrasonic) in step 150. In step 151, a path is traced on the skin of the patient and/or coordinates of the three-dimensional path geometry of the vessel are stored in a processor (e.g., computer memory). During tunnel dissection, external images showing the endoscopic instrument (e.g., dissector), the patient/subject, and the traced path are captured in step 152.

Using the captured images, the controller estimates a location of the head (distal end) of the dissector in step 153 based on the portion of the dissector that remains visible outside the patient, for example. The estimated head location is compared to the pre-mapped path in step 154. A check is performed in step 155 to determine whether the head location is within a selected boundary (e.g., within a threshold distance) of the pre-mapped path. If within the boundary, then a return is made to step 152 to continue monitoring progress. If not within the desired boundaries, then a warning is provided to the user in step 156.

What is claimed is:

1. A method of guiding endoscopic vessel harvesting to remove a blood vessel or vessel section to be used as a bypass graft, the method comprising the steps of:

pre-mapping a dissection path of a vessel to be harvested using transcutaneous sensing of the vessel;

dissecting, using a dissector, a working tunnel along the vessel to be harvested, wherein the working tunnel is a dissected tunnel;

capturing a series of images from an endoscopic camera at a distal tip of an endoscopic instrument within the dissected tunnel, wherein the dissected tunnel is formed around the vessel to be harvested, and wherein the vessel is within a limb of a patient;

estimating relative distances between trackable features present in more than one image of the series of images;

assembling a three-dimensional model of the dissected tunnel from the series of images captured by the endoscopic camera, the three-dimensional model based on the estimated relative distances;

rendering a consolidated map representing the three-dimensional model on a display visible to a user;

rendering a marker on the display in association with the map indicating a current location of the distal tip;

comparing a current location of the distal tip with the dissection path; and presenting a warning to the user when a deviation between the current location of the distal tip and the dissection path exceeds a predetermined threshold.

2. The method of claim 1 wherein the display is comprised of an augmented-reality display.

3. The method of claim 1, wherein the step of assembling the three-dimensional model is comprised of:

locating the distal tip at a starting location in the dissected tunnel;

analyzing a corresponding captured image to extract at least a first feature;

moving the distal tip along the dissected tunnel away from the starting location;

tracking a changing position of the first feature in subsequent images of the series of images;

extracting a second feature in one of the subsequent images and tracking a changing position of the second feature in additional subsequent images; and linking the extracted features according to the changing positions to define the three-dimensional model.

4. The method of claim 1 further comprising the step of:

rendering at least one size marker in association with the map on the display to indicate a corresponding length of at least a portion of the three-dimensional model.

5. The method of claim 1 further comprising the steps of:

rendering an instantaneous endoscopic image on the display; and rendering an actual size indicator of at least one visible structure in the instantaneous endoscopic image.

6. The method of claim 1 further comprising the steps of:

rendering an instantaneous endoscopic image on the display; and rendering a depth indicator of at least one visible structure in the instantaneous endoscopic image.

7. The method claim 6 wherein the depth indicator specifies a relative depth relationship between at least two visible structures, wherein one visible structure is indicated as a foreground structure, and wherein another visible structure is indicated as a background structure.

8. The method of claim 1 further comprising the steps of:

rendering an instantaneous endoscopic image on the display;

identifying a side branch to the vessel using image analysis; and rendering a side branch indicator to highlight the identified side branch on the display of the instantaneous endoscopic image.

9. The method of claim 1 wherein the display is comprised of an augmented-reality display, and wherein the method further comprises the steps of:

taking an action, by the user, to indicate a screen update command while continuously holding the endoscopic instrument;

sensing the screen update command; and selecting data to display on the augmented-reality display in response to the screen update command.

10. The method of claim 1, wherein the display comprises an augmented-reality display, and wherein the user wears the augmented-reality display when the user dissects the working tunnel around the vessel.

11. The method of claim 1, wherein dissecting the working tunnel comprises positioning the dissector externally along the vessel, wherein the vessel is connected to peripheral tissue, and separating, by dissection, the peripheral tissue from the vessel using the dissector.

12. The method of claim 1, comprising inserting the endoscopic instrument into an incision above the vessel to be harvested before dissecting the working tunnel.

* * * * *